United States Patent
Richard

(10) Patent No.: US 9,315,807 B1
(45) Date of Patent: Apr. 19, 2016

(54) GENOME SELECTION AND CONVERSION METHOD

(71) Applicant: Directed Genomics, LLC, Toney, AL (US)

(72) Inventor: Cynthia L. Richard, Toney, AL (US)

(73) Assignee: New England Biolabs, Inc., Ipswich, MA (US)

( * ) Notice: Subject to any disclaimer, the term of this patent is extended or adjusted under 35 U.S.C. 154(b) by 51 days.

(21) Appl. No.: 14/163,885

(22) Filed: Jan. 24, 2014

Related U.S. Application Data

(60) Provisional application No. 61/757,119, filed on Jan. 26, 2013.

(51) Int. Cl.
| | |
|---|---|
| *C12Q 1/68* | (2006.01) |
| *C40B 30/04* | (2006.01) |
| *C40B 50/06* | (2006.01) |
| *C12N 15/10* | (2006.01) |

(52) U.S. Cl.
CPC .......... *C12N 15/1072* (2013.01); *C12Q 1/6806* (2013.01); *C12Q 1/6869* (2013.01); *C40B 30/04* (2013.01); *C40B 50/06* (2013.01)

(58) Field of Classification Search
None
See application file for complete search history.

(56) References Cited

U.S. PATENT DOCUMENTS

| | | |
|---|---|---|
| 2003/0096232 A1 | 5/2003 | Kris et al. |
| 2008/0050735 A1 | 2/2008 | Pushnova |
| 2010/0029498 A1* | 2/2010 | Gnirke et al. ............... 506/9 |

FOREIGN PATENT DOCUMENTS

| | | |
|---|---|---|
| WO | WO 97/47640 | 12/1997 |
| WO | WO 99/36571 | 7/1999 |
| WO | WO 02/16647 | 8/2002 |
| WO | WO 2011/056863 | 5/2011 |

OTHER PUBLICATIONS

Bourzac, et al., Journal of Biotechnology, 154, 68-75 (2011).
Okou, et al., Nature Methods, 4, 11, 907-909 (2007).
International Search Report and Written Opinion of the International Searching Authority for Application No. PCT/US2014/031222 dated Jul. 18, 2014.

* cited by examiner

*Primary Examiner* — Samuel Woolwine
*Assistant Examiner* — Kaijiang Zhang
(74) *Attorney, Agent, or Firm* — New England Biolabs, Inc.; Harriet M. Strimpel

(57) ABSTRACT

The present disclosure provides a method and a kit for selecting and enriching target sequences specific for one or more genomic regions of interest or a subset of a transcriptome using a target-capturing library of probes. The target-enriched library is generated from a random pool of deoxyribonucleic acid (DNA) fragments. The present disclosure provides an efficient and cost-effective method of target selection for targeted genome sequencing, targeted nucleic acid library creation and gene expression studies.

1 Claim, No Drawings

SEQUENCE LISTING

<160> NUMBER OF SEQ ID NOS: 8

<210> SEQ ID NO 1

```
<211> LENGTH: 51
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (35)..(42)
<223> OTHER INFORMATION: n is a, c, g, or t

<400> SEQUENCE: 1
agatcggaag agcacacgtc tgaactccag tcacnnnnn nnatctcgta t            51

<210> SEQ ID NO 2
<211> LENGTH: 50
<212> TYPE: DNA
<213> ORGANISM: Artificial Sequence
<220> FEATURE:
<223> OTHER INFORMATION: Synthetic construct

<400> SEQUENCE: 2
tctagccttc tcgtgtgcag acttgaggtc agtggttcgt ccttctgccg             50

<210> SEQ ID NO 3
<211> LENGTH: 66
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (35)..(42)
<223> OTHER INFORMATION: n is a, c, g, or t

<400> SEQUENCE: 3
agatcggaag agcacacgtc tgaactccag tcacnnnnnn nnatctcgta tgccgtcttc  60
tgcttg                                                            66

<210> SEQ ID NO 4
<211> LENGTH: 33
<212> TYPE: DNA
<213> ORGANISM: Artificial Sequence
<220> FEATURE:
<223> OTHER INFORMATION: Synthetic construct

<400> SEQUENCE: 4
ctagccttct cgtgtgcaga cttgaggtca gtg                               33

<210> SEQ ID NO 5
<211> LENGTH: 67
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (29)..(34)
<223> OTHER INFORMATION: n is a, c, g, or t

<400> SEQUENCE: 5
atgatacggc gaccaccgag atctacacnn nnnnacactc tttccctaca cgacgctctt  60
ccgatct                                                           67

<210> SEQ ID NO 6
```

```
<211> LENGTH: 68
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (30)..(36)
<223> OTHER INFORMATION: n is a, c, g, or t

<400> SEQUENCE: 6
ttactatgcc gctggtggct ctagatgtgn nnnnntgtga gaaagggatg tgctgcgaga      60
aggctaga                                                              68

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
aatgatacgg cgaccaccga                                                 20

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
agcatacggc agaagacgaa c                                               21
```

GENOME SELECTION AND CONVERSION METHOD

BACKGROUND

Current technology for analysis of known, suspected or hypothesized genes requires the creation of a DNA library prior to enrichment with target probes or baits. Note that target probes or baits are mechanisms for capturing specific nucleic acids or other molecule of interest from a molecular pool. The creation of the DNA library is time consuming, results in sample loss and the need for amplification prior to enrichment, and generates a library that contains the regions of interest at undefined locations within the fragments.

SUMMARY

The methods described in the present disclosure enrich target DNA/RNA sequences from a nucleic acid sample to create a target-enriched deoxyribonucleic acid (DNA) and/or ribonucleic acid (RNA) library. The target-enriched DNA library is generated by randomly fragmenting a pool of nucleic acids, for example, genomic DNA from a eukaryotic organism, adding target probes for the target sequences and enzymes to remove non-target nucleic acid, thereby isolating the target of interest in the nucleic acid sample, and creating a DNA/RNA library from only the target or targets of interest in the nucleic acid sample. The methods can be applied for both genome and transcriptome target selection and enrichment. In addition to capturing target sequences, the methods can also be applied to remove target nucleic acid sequences from a nucleic acid sample. One possible use of these methods can be for gene expression studies in determining disease or condition specific transcripts from a sample.

The target sequences used herein refer to nucleic acid sequences containing sequences of interest. A target sequence can be an exon, a long stretch of genomic sequence, a complementary deoxyribonucleic acid (cDNA) sequence, or short DNA fragments of the region of interest. The target sequences particularly referred to are short DNA sequences generated from a region of interest that may be sequenced. The target sequences constitute a subset of an entire sample of nucleic acids or genomic DNA, where a researcher or person wishes to isolate and/or enrich the target sequences for further studies. A target template includes a continuous region of a DNA sequence or a collection of DNA sequences (e.g. cDNA sequences) or DNA extracted from a source that may include all variations or anomalous target sequences. A target template can also be RNA sequences, for example, ribosomal ribonucleic acid (rRNA) sequences, messenger ribonucleic acid (mRNA) sequences, small interfering ribonucleic acid (siRNA) sequences, small nuclear ribonucleic acid (snRNA) sequences, or any other type of RNA extracted from any source. A target fragment includes target sequences of interest and nucleic acid sequences that are not of interest. A target-isolation sequence is an artificially or otherwise created, made or obtained short stretch of nucleic acids that does not originate from the sample nucleic acids where the target-isolation sequence acts as a probe.

The methods of the present disclosure target and isolate target templates from a randomly fragmented purified source prior to creating a DNA/RNA library to generate a pool of overlapping and/or target sequence fragments that collectively cover the whole targeted region of interest in an unbiased way, which can then be then be used to create a targeted DNA/RNA library or in other ways, such as removal of the whole targeted region of interest prior to creation of a DNA/RNA library.

In one embodiment, the method of selecting and enriching target templates from a nucleic acid sample comprises the following steps: a) obtaining a purified nucleic acid sample that encompasses all the sequences of the target sequences of interest; b) hybridizing said nucleic acid sample with one or more target-isolation sequences; c) capturing the hybrids of the target-isolation sequences and the target fragment; d) removing non-targeted randomly fragmented nucleic acids from the target fragments; e) adding adaptors to one or both ends of a target templates; and f) amplifying the library of target templates of random DNA/RNA fragments. The method of selecting and enriching target templates from a nucleic acid sample can use one or more target isolation sequences either during one hybridization step or multiple hybridization steps.

The random fragments of nucleic acids can be created using enzymatic methods, including, but not limited to, using a single or a combination of nucleases such as Fragmentase™ (NEB, Ipswich, Mass.), DNAse I, and Benzonase® (EMD, Gibbstown, N.J.), and other types of nucleases. Fragmentase™ is an endonuclease that generates double-stranded DNA (dsDNA) breaks in a time-dependent manner to yield 100-800 base-pair (bp) DNA fragments. Benzonase® is genetically engineered endonuclease from *Serratia marcescens* that can effectively cleavage both DNAs and RNAs.

A capture domain of the target-isolation sequence refers to a chemical structure or moiety attached, linked to or adjacent to the target-isolation sequence; and the chemical structure or moiety comprises an affinity binding group (e.g. a biotin, an antigen, a ligand, which allows the capture of the capture domain and nucleic acid sequence through association of a second domain) or a cross-linking moiety (e.g. a modified nucleotide capable of photochemically or chemically forming a covalent bond to substrates). A target-isolation sequence hybridizes to the target template allowing the target template to be isolated and separated from non-target sequence fragments.

In some embodiments, the target-isolation sequence may first hybridize to target sequences of the target fragments in solution where the hybrids are then separated from the non-target nucleic acid fragments in a nucleic acid sample through the association of the capture domain to a second domain. In another embodiment, the target-isolation sequences can first be immobilized to a solid or permeable structure through or in association with the capture domain. Immobilized target-isolation sequences are then hybridized with target fragments and capture the target fragments onto the solid support. The target-isolation sequences can be DNA sequences or RNA sequences.

In some embodiments, random fragments of nucleic acids are generated from a nucleic acid sample that encompasses all the sequences of the target sequences of interest and includes non-target sequences using physical means, including, but not limited to, sonication, nebulization, physical shearing, and heating.

The target template can be an RNA sequence. An advantage of using RNA as a target template is that the target template does not contain non-target sequences. The target RNA template may be broken into random fragments of RNA using enzymatic and/or physical means.

Another embodiment of the present disclosure is a kit for selecting and enriching target templates from a nucleic acid sample where the nucleic acid sample contains non-target and target sequences, comprising: target-isolation sequences, either defined by the creator or manufacturer of the kit or by a researcher, where the target-isolation sequences include a capture domain; a second domain; adaptors; nucleases; and blocking nucleic acid sequences, hereinafter referred to as "blocking sequences", where a blocking nucleic sequence is a short nucleic acid sequence not part of the sample or source nucleic acids and artificially created and where the nucleic acid sequence does not hybridize to the target template. The capture domain may comprise an affinity binding group or a crosslinking moiety. The second domain can bind to the capture domain by affinity binding or form a covalent bond with the crosslinking moiety of the capture domain. For example, the capture domain may have a biotin moiety and the second domain is streptavidin. The kit may further comprise one or more buffer solutions and standard solutions for the creation of a DNA library.

DETAILED DESCRIPTION

The present disclosure provides a method for making a targeted DNA library specific for one or more DNA regions or a subset of transcriptome using a pool of target-isolation probes. In this regard, the present disclosure describes a method for (1) using a capture domain on the target-isolation probes that allows hybridization between the target isolation probe and target template to be separated from non-target template; (2) using nucleases to remove non-target sequences from a target fragment; (3) using blocking nucleic acids to prevent annealing of the randomly fragmented nucleic acids to other randomly fragmented nucleic acids that can be specifically digested prior to using nucleases to remove non-target sequences from target fragments; and (4) using target-isolation probes to create a DNA library containing target sequences from both strands. The present disclosure provides an efficient and cost-effective method for creating DNA libraries with the targets of interest.

The terms "target sequences" or "target nucleic acids" are used interchangeably, and refer to any fragment of a region of interest. Target sequences may be, for example, nucleic acid sequences, an exon (i.e., a segment of DNA or RNA molecule), a stretch of genomic sequence, a cDNA sequence, and/or any fragment of the region of interest. Other exemplary targets of interest may include, but are not limited to, those associated with one or more diseases, a signaling pathway, a genomic region, a regulatory region, and/or a group of related genes.

The term "nucleic acid sample" as used in this application refers to DNA or RNA sequences obtained from any source, where the sequences are a mixture of sequences with target sequences and non-target sequences. For example, a nucleic acid sample can be obtained from artificial sources, cells, tissues, organs, and any other biological and environmental sources. A nucleic acid sample may comprise whole genomic sequences, part of the genomic sequence, chromosomal sequences, polymerase chain reaction (PCR) products, cDNA sequences, mRNA sequences or whole transcriptome sequences. The target sequences of interest are only a subset of a nucleic acid sample.

The term "a target template" as used in this application, refers to DNA/RNA sequences that collectively cover the whole range or a substantial portion of all the target sequences of interest. A target template does not necessarily have exactly the same sequence as target sequences. Target sequences may have sequence mutations that are different from the target template (e.g. single nucleotide polymorphism). A target template can be a continuous region of a DNA sequence, a collection of DNA sequences or DNA extracted from any source. A target template can also be RNA sequences, for example, rRNAs, mRNAs, siRNAs, and snRNA. Target sequences isolated and enriched from one source using the method in this application can act to reconstruct an entire target template.

The term "random DNA/RNA fragments" as used herein, refers to a portion or a segment of a larger DNA or RNA sequence that is cleaved or released from the larger DNA or RNA sequence at random or almost random locations. The process of generating smaller fragments from a larger nucleic acid sequence is also referred to as "fragmenting." Random DNA/RNA fragments can be generated by enzymatic or physical means.

The term "target-isolation sequences" as used herein, refers to nucleic acid sequences comprising sequences substantially complimentary to target sequences. The target-isolation sequences have a capture domain or are capable of linking to a capture domain allowing the isolation and separation of target-isolation sequences and their associated target sequences.

The term "capture domain" as used herein, refers to a structure or a moiety associated with, linked or adjacent to a target-isolation sequence where the capture domain containing target-isolation sequence and the target template can be separated from the rest of non-target containing random DNA/RNA fragments. The capture domain can be an affinity binding group allowing the capture of the capture domain containing target-isolation sequence by affinity binding to a second domain, or a cross-linking moiety.

In accordance with an embodiment of the present disclosure, one method for isolating and preparing libraries of target nucleic acid sequences uses a target isolation sequence and a second probe. In such an embodiment, the method of selecting and enriching target sequences from a pool of random DNA fragments, comprises: a) extracting and fragmenting nucleic acid sequences from a source or sample of interest; b) designing and preparing target-isolation sequences and associating the target-isolation sequences with a capture domain; c) mixing, in a solution, the random DNA fragments with the target-isolation sequences where the conditions of the solution allow the target-isolation sequences and the target fragments to hybridize; d) capturing the hybrids of the target-isolation sequences and the target fragments and separating the hybrids from non-target random DNA fragments; e) removing one or more nucleic acids from the target fragments where the removed nucleic acids do not correspond to the target sequences; and f) using the isolated target templates to create a target DNA library.

First, nucleic acid sequences from sources of interest are extracted and purified from sources of interest where the nucleic acid sequences are hypothesized to contain the target sequences. For DNA extraction from cells, the cells are first breached or broken apart either physically by using, for example, the use of small beads at high velocities, or chemically by using, for example, detergents and other surfactants. An alcohol or other chemical is used for precipitating the DNA. The purified DNA is then treated, creating a pool of random DNA fragments.

Next, the random DNA fragments are combined with artificially created RNA sequences where these RNA sequences are complementary to repetitive sequences found in DNA. The artificially created RNA sequences are hereinafter referred to as "blocking RNA." The random DNA fragments and blocking RNA are heated to allow denaturation of the random DNA fragments and blocking RNA and then cooled to allow the blocking RNA to hybridize to the random DNA fragments. 3' target-isolation sequences, with a biotin domain, are designed from the target sequences, where the 3' target-isolation sequences are substantially complementary to the 3' ends of the target sequences. The 3' target-isolation sequences included a modification to its 5' end that inhibited nuclease digestion and a 3' modification that inhibited nuclease digestion, polymerase extension, and ligation.

The target-isolation sequences are then added to a hybridization solution containing the pool of random DNA fragments. The hybridization solution containing the 3' target-isolation sequences and random DNA fragments is then incubated to allow one or more copies of the 3' target-isolation sequences to hybridize to one or more copies of the target fragments. In one embodiment, hybridization conditions consist of a hybridization buffer, e.g., 5× Saline-Sodium Phosphate-EDTA Buffer (SSPE), 5× Deinhardt's, 0.1% Sodium Dodecyl Sulfate SDS. Other hybridization buffers may be used in other embodiments. In one embodiment, a hybridization period may be, for example, sixteen (16) hours. However, such hybridization period may be greater or less in other embodiments depending upon the hybridization conditions.

A plurality of magnetic beads coated in streptavidin is added after the hybridization incubation. The hybridization solution is then incubated for approximately 30 minutes at ambient temperature. The plurality of magnetic beads is first isolated in the mixture using a magnetic source then separated from the hybridization solution, with the hybridization solution and non-target fragments discarded. The plurality of magnetic beads associated with one or more of the 3' target isolation sequences hybridized to one or more of the template fragments are washed with a buffer.

The plurality of magnetic beads is then combined with a 3' nuclease reaction buffer containing RNase H and one or more single-stranded 3' exonucleases, such as Exonuclease I and/or Exonuclease T, to create a 3' digestion solution. The 3' digestion solution is then incubated for approximately one hour at approximately 20° C. The plurality of magnetic beads is separated from the 3' digestion solution by a magnetic source and the 3' digestion solution is discarded. The magnetic beads are then resuspended in a dA-tailing buffer [10 mM Tris-HCl, 10 mM MgCl$_2$, 50 mM NaCl, 1 mM DTT, 0.2 mM dATP]. 3' to 5' exo-Klenow fragment is added to the dA-tailing mixture and the mixture is incubated for 30 minutes at 37° C., which allowed the addition of a dA-tail to 3' end of the target fragments. The plurality of magnetic beads is then isolated from the dA-tailing mixture using a magnetic source and separated from the dA-tailing mixture solution, with the dA-tailing mixture being discarded. The plurality of beads are washed in a buffer and then resuspended in a ligation buffer [66 mM Tris-HCl, 10 mM MgCl$_2$, 1 mM DTT, 1 mM ATP, 6% PEG 8000, pH 7.6].

A 3' adaptor sequence and T4 DNA ligase are added to the ligation mixture. In one embodiment, the 3' adaptor sequence is a single-strand hairpin 3' adaptor containing a cleavable nucleic acid base of dU, but can also contain a cleavable 8-oxo-G or a double strand with at least one double-stranded region with a terminal protector group that inhibits exonucleases activity. The 3' adaptor sequence contained an NGS platform-specific sequencing primer site, a library amplification primer site and a unique strand identifier sequence. The plurality of magnetic beads is then isolated from the ligation mixture using a magnetic source and separated from the ligation mixture, with the ligation mixture being discarded.

The plurality of magnetic beads are then washed with a buffer and resuspended in 3'-double-stranded (ds)-exonuclease buffer [10 mM Tris-HCl, 50 mM NaCl, 10 mM MgCl$_2$, 1 mM DTT, pH 7.9]. A double-stranded 3'-exonuclease, is added, e.g., T4 DNA polymerase, and the exonuclease mixture is incubated for 30 minutes at 20° C., thus removing any remaining non-target sequences with unprotected 3' ends. The plurality of magnetic beads is then isolated from the exonuclease mixture using a magnetic source and separated from the exonuclease mixture, with the exonuclease mixture being discarded.

The plurality of magnetic beads are then washed with a buffer and resuspended in 5'-hybridization buffer [12 mM Tris-HCl, 60 mM NaCl, 12 mM Mg Cl$_2$, 1 mM DTT, pH 7.9]. 5' nucleic acid probes, hereinafter the 5' end capture probes, substantially complementary to the 5' end of the target sequences are added to the 5'-hybridization mixture. In one embodiment, as a 3' hairpin adaptor sequence is used, the 5'-hybridization mixture is heated to 95° C. and slowly cooled to room temperature. In another embodiment, a 3' double stranded adaptor may be used. In such an embodiment, the 5' hybridization mixture is heated to 65° C. and then slowly cooled to room temperature. The plurality of magnetic beads is then isolated from the 5'-hybridization mixture using a magnetic source and separated from the 5'-hybridization mixture, with the 5'-hybridization mixture being discarded.

The plurality of magnetic beads are then washed with a buffer and resuspended in 5'-single-stranded (ds)-nuclease buffer [10 mM Tris-HCl, 50 mM NaCl, 10 mM Mg Cl$_2$, 1 mM DTT, pH 7.9]. A 5' nuclease is added, e.g., RecJ. In other embodiments, one or more 5' nucleases may be added to the nuclease mixture. The nuclease mixture is incubated for 30 minutes at 37° C. The temperature is then reduced to 20° C. and a dNTP mix and T4 DNA polymerase are added to the nuclease mixture. The nuclease mixture is incubated for an additional 30 minutes. The plurality of magnetic beads is then isolated from the 5'-nuclease mixture using a magnetic source and separated from the 5'-nuclease mixture, with the 5'-nuclease mixture being discarded.

The plurality of magnetic beads is then washed with a buffer and resuspended in a second ligation buffer [66 mM Tris-HCl, 10 mM MgCl$_2$, 1 mM DTT, 1 mM ATP, 6% PEG 8000, pH 7.6]. A 5' adaptor sequence, with at least one double stranded region, and T4 DNA ligase are then added and the second ligation mixture is incubated for 15 minutes at ambient temperature. The 5' adaptor sequence contained an NGS platform-specific sequencing primer site, a library amplification site and a barcode sequence for sample identification. The plurality of magnetic beads is then isolated from the second ligation mixture using a magnetic source and separated from the second ligation mixture, with the second ligation mixture being discarded.

The plurality of magnetic beads is then washed with a buffer and resuspended in a PCR mixture containing water, a PCR master mix and amplification primers. If the hairpin contains 8-oxo-G, formamidopyrimidine [fopy]-DNA glycosylase (Fpg) and Endonuclease VIII are added. Alternatively, if the hairpin contains dU USER™ enzyme (Uracil-Specific Excision Reagent, NEB, MA) is added. The PCR mixture is incubated at 37° C. for 20 minutes and following PCR cycling conditions is used: 95° C. for 2 minutes followed by 15 cycles of 95° C. for 30 seconds, 60° C. for 30 seconds and 72° C. for 1 minute. At the end of the 15 cycles, the PCR mixture incubated at 72° C. for 5 minutes. The PCR products obtained from the target sequences are then sequenced using conventional methods.

In accordance with an embodiment of the present disclosure, another method for isolating and preparing libraries of target nucleic acid sequences uses a 5' flap endonuclease. In such an embodiment, nucleic acid sequences from sources of interest are extracted and purified from sources of interest where the nucleic acid sequences are hypothesized to contain the target sequences. For DNA extraction from cells, the cells are first breached or broken apart either physically by using, for example, the use of small beads at high velocities, or chemically by using, for example, detergents and other surfactants. An alcohol or other chemical is used for precipitating the DNA. The purified DNA is then treated, creating a pool of random DNA fragments.

Next, the random DNA fragments are combined with artificially created RNA sequences where these RNA sequences are complementary to repetitive sequences found in DNA. The artificially created RNA sequences are hereinafter referred to as "blocking RNA." The random DNA fragments and blocking RNA are heated to allow denaturation of the random DNA fragments and blocking RNA and then cooled to allow the blocking RNA to hybridize to the random DNA fragments. 3' target-isolation sequences, with a biotin domain, are designed from the target sequences, where the 3' target-isolation sequences are substantially complementary to the 3' end of the target sequences. The 3' target-isolation sequences included a modification to its 5' end that inhibited nuclease digestion and a 3' modification that inhibited nuclease digestion, polymerase extension, and ligation.

The target-isolation sequences are then added to a hybridization solution containing the pool of random DNA fragments. The hybridization solution containing the 3' target-isolation sequences and random DNA fragments is then incubated to allow one or more copies of 3' target-isolation sequences to hybridize to one or more copies of the target fragments. In one embodiment, hybridization conditions consist of a hybridization buffer, e.g., e.g., 5×SSPE, 5× Deinhardt's, 0.1% SDS. Other hybridization buffers may be used in other embodiments. In one embodiment, a hybridization period may be, for example, sixteen (16) hours. However, such hybridization period may be greater or less in other embodiments depending upon the hybridization conditions.

A plurality of magnetic beads coated in streptavidin is added after the hybridization incubation. The hybridization solution is then incubated for approximately 30 minutes at ambient temperature. The plurality of magnetic beads is first isolated in the mixture using a magnetic source then separated from the hybridization solution, with the hybridization solution and non-target fragments discarded. The plurality of magnetic beads associated with one or more of the 3' target isolation sequences hybridized to one or more of the template fragments is washed with a buffer.

The plurality of magnetic beads is then combined with a 3' nuclease reaction buffer containing RNase H and one or more single-stranded 3' exonucleases, such as Exonuclease I and/or Exonuclease T, to create a 3' digestion solution. The 3' digestion solution is then incubated for approximately one hour at approximately 20° C. The plurality of magnetic beads is separated from the 3' digestion solution by a magnetic source and the 3' digestion solution is discarded. The magnetic beads are then resuspended in a dA-tailing buffer [10 mM Tris-HCl, 10 mM MgCl$_2$, 50 mM NaCl, 1 mM DTT, 0.2 mM dATP]. 3' to 5' exo-Klenow fragment is added to the dA-tailing mixture and the mixture is incubated for 30 minutes at 37° C., which allowed the addition of a dA-tail to 3' end of the target fragments. The plurality of magnetic beads is then isolated from the dA-tailing mixture using a magnetic source and separated from the dA-tailing mixture solution, with the dA-tailing mixture being discarded. The plurality of beads are washed in a buffer and then resuspended in a ligation buffer [66 mM Tris-HCl, 10 mM MgCl$_2$, 1 mM DTT, 1 mM ATP, 6% PEG 8000, pH 7.6].

A 3' adaptor sequence and T4 DNA ligase are added to the ligation mixture. In one embodiment, the 3' adaptor sequence is a single-strand hairpin 3' adaptor containing a cleavable nucleic acid base of dU. In other embodiments, the 3' adaptor may contain a cleavable 8-oxo-G or a double strand with at least one double-stranded region with a terminal protector group that inhibits exonucleases activity. In one embodiment, the 3' adaptor sequence contains an NGS platform-specific sequencing primer site, a library amplification primer site and a unique strand identifier sequence. The plurality of magnetic beads is then isolated from the ligation mixture using a magnetic source and separated from the ligation mixture, with the ligation mixture being discarded.

The plurality of magnetic beads are then washed with a buffer and resuspended in 3'-double-stranded (ds)-exonuclease buffer [10 mM Tris-HCl, 50 mM NaCl, 10 mM Mg Cl$_2$, 1 mM DTT, pH 7.9]. A double-stranded 3'-exonuclease, e.g., T4 DNA polymerase, is added, and the exonuclease mixture is incubated for 30 minutes at 20° C. Incubation removes any remaining non-target sequences with unprotected 3' ends. The plurality of magnetic beads is then isolated from the exonuclease mixture using a magnetic source and separated from the exonuclease mixture, with the exonuclease mixture being discarded.

The plurality of magnetic beads are then washed with a buffer and resuspended in 5'-hybridization buffer [12 mM Tris-HCl, 60 mM NaCl, 12 mM Mg Cl$_2$, 1 mM DTT, pH 7.9]. A 5' flap capture probe, where the 5' capture probe contains a single-stranded 5' region and a double-stranded 3' region, is added to the 5'-hybridization mixture. The 5' region is substantially complementary to the 5' end of the target sequence. The double-stranded 3' region is formed by a hairpin structure on the 3' end of the probe. In one embodiment, the double-stranded 3' region contains an NGS platform-specific sequencing primer site, a library amplification site and a barcode sequence for sample identification. In other embodiments, the double-stranded 3' end may be formed by addition a short, complementary strand to the 3' end of the probe. In such an embodiment, when a 3' hairpin adaptor sequence is used, the 5'-hybridization mixture is heated to 95° C. and slowly cooled to room temperature. If a 3' double stranded adaptor is used, the 5'-hybridization mixture is heated to 65° C. and then slowly cooled to room temperature. The plurality of magnetic beads is then isolated from the 5'-hybridization mixture using a magnetic source and separated from the 5'-hybridization mixture, with the 5'-hybridization mixture being discarded.

The plurality of magnetic beads are then washed with a buffer and resuspended in 5'-single-stranded (ds)-nuclease buffer [10 mM Tris-HCl, 50 mM NaCl, 10 mM Mg Cl$_2$, 1 mM DTT, pH 7.9]. A flap endonuclease is added, e.g., Fen-1, and T4 DNA ligase. Other nucleases are possible in other embodiments. The nuclease mixture is incubated for 1 hour at 25° C. The plurality of magnetic beads is then isolated from the 5'-nuclease mixture using a magnetic source and separated from the 5'-nuclease mixture, with the 5'-nuclease mixture being discarded.

The plurality of magnetic beads is then washed with a buffer and resuspended in a PCR mixture containing water, a PCR master mix and amplification primers. In one embodiment, where a 3' adaptor sequence with a hairpin with dU is used, USER enzyme is added to the PCR mixture. If the hairpin contains 8-oxo-G, Fpg and Endonuclease VIII are added instead of USER enzyme. The PCR mixture is incubated at 37° C. for 20 minutes and the following PCR cycling conditions are used: 95° C. for 2 minutes followed by 15 cycles of 95° C. for 30 seconds, 60° C. for 30 seconds and 72° C. for 1 minute. At the end of the 15 cycles, the PCR mixture is incubated at 72° C. for 5 minutes and then held at 4° C. until purified. The PCR products from the PCR mixture are purified using a PCR clean up column from Qiagen. The PCR products obtained from the target sequences are then sequenced.

In accordance with an embodiment of the present disclosure, another method for isolating and preparing libraries of target nucleic acid sequences uses one target isolation sequence. In such an embodiment, nucleic acid sequences from sources of interest are extracted and purified from sources of interest where the nucleic acid sequences are hypothesized to contain the target sequences. For DNA extraction from cells, the cells are first breached or broken apart either physically by using, for example, the use of small beads at high velocities, or chemically by using, for example, detergents and other surfactants. An alcohol or other chemical is used for precipitating the DNA. The purified DNA is then physically treated, creating a pool of random DNA fragments.

Next, the random DNA fragments are combined with artificially created RNA sequences where these RNA sequences are complementary to repetitive sequences found in DNA. The artificially created RNA sequences are hereinafter referred to as "blocking RNA." The random DNA fragments and blocking RNA are heated to allow denaturation of the random DNA fragments and blocking RNA and then cooled to allow the blocking RNA to hybridize to the random DNA fragments.

Target-isolation sequences, with a biotin domain, are designed from the target sequences, where the target-isolation sequences are substantially complementary to the target sequence. The target-isolation sequences included a modification to the 5' end that inhibited nucleases from digesting the target-isolation sequences. In one embodiment, hybridization conditions consist of a hybridization buffer, e.g., 5×SSPE, 5× Deinhardt's, 0.1% SDS. Other hybridization buffers may be used in other embodiments. In one embodiment, a hybridization period may be, for example, sixteen (16) hours. However, such hybridization period may be greater or less in other embodiments depending upon the hybridization conditions.

The target-isolation sequences are then added to a hybridization solution containing the pool of random DNA fragments. The hybridization solution containing the target-isolation sequences and random DNA fragments with subsections of the random DNA fragments hybridized to the blocking RNA is then incubated to allow one or more copies of the target-isolation sequences to hybridize to one or more copies of a target fragments. A plurality of magnetic beads coated in streptavidin is added after the hybridization incubation. The hybridization solution is then incubated for approximately 30 minutes at ambient temperature. The plurality of magnetic beads is first isolated in the mixture using a magnetic source then separated from the hybridization solution, with the hybridization solution and non-target fragments discarded.

The plurality of magnetic beads, now associated with one or more of the target isolation sequences hybridized to one or more of the template fragments, are then washed with a buffer and resuspended in an exonuclease buffer [10 mM Bis-Tris-Propane, 10 mM Mg $Cl_2$, 1 mM DTT, pH 7.0]. RNase H, one or more single stranded 3' exonucleases (in one embodiment, Exonuclease T and Exonuclease I are added) and one or more single stranded 5' nucleases (in one embodiment, RecJ and Exonuclease VII) are added to the exonuclease mixture. The exonuclease mixture is incubated for 30 minutes at 25° C. The plurality of magnetic beads is then isolated from the exonuclease mixture using a magnetic source and separated from the exonuclease mixture, with the exonuclease mixture being discarded.

The magnetic beads are then resuspended in a dA-tailing buffer [10 mM Tris-HCl, 10 mM $MgCl_2$, 50 mM NaCl, 1 mM DTT, 0.2 mM dATP]. 3' to 5' exo-Klenow fragment is added to the dA-tailing mixture and the mixture is incubated for 30 minutes at 37° C., which allowed the addition of a dA-tail to 3' end of the target fragments. The plurality of magnetic beads is then isolated from the dA-tailing mixture using a magnetic source and separated from the dA-tailing mixture solution, with the dA-tailing mixture being discarded. The plurality of beads are washed in a buffer and then resuspended in a ligation buffer [66 mM Tris-HCl, 10 mM $MgCl_2$, 1 mM DTT, 1 mM ATP, 6% PEG 8000, pH 7.6].

A 3' adaptor sequence and T4 DNA ligase were added to the ligation mixture. In one embodiment, the 3' adaptor sequence is a double strand with at least one double-stranded region with a terminal protector group that inhibits exonucleases activity. The 3' adaptor sequence contained an NGS platform-specific sequencing primer site, a library amplification primer site and a unique strand identifier sequence. The ligation mixture is incubated at ambient temperature for 15 minutes. The plurality of magnetic beads is then isolated from the ligation mixture using a magnetic source and separated from the ligation mixture, with the ligation mixture being discarded.

The plurality of magnetic beads are then washed in a buffer and resuspended in a repair buffer [10 mM Tris-HCl, 50 mM NaCl, 10 mM Mg $Cl_2$, 1 mM DTT, 0.4 mM each of dNTPs, pH 7.9]. T4 DNA polymerase is added and the repair mixture incubated at ambient temperature for 30 minutes. The plurality of magnetic beads is then isolated from the repair mixture using a magnetic source and separated from the repair mixture, with the repair mixture being discarded.

The plurality of magnetic beads is then washed with a buffer and resuspended in a ligation buffer [66 mM Tris-HCl, 10 mM $MgCl_2$, 1 mM DTT, 1 mM ATP, 6% PEG 8000, pH 7.6]. A 5' adaptor sequence, with at least one double stranded region, and T4 DNA ligase are then added and the ligation mixture is incubated for 15 minutes at ambient temperature. The 5' adaptor sequence contained an NGS platform-specific sequencing primer site, a library amplification site and a barcode sequence for sample identification. The plurality of magnetic beads is then isolated from the ligation mixture using a magnetic source and separated from the ligation mixture, with the ligation mixture being discarded.

The plurality of magnetic beads is then washed with a buffer and resuspended in a PCR mixture containing water, a PCR master mix and amplification primers. The PCR cycling conditions are used as follows: 95° C. for 2 minutes followed by 15 cycles of 95° C. for 30 seconds, 60° C. for 30 seconds and 72° C. for 1 minute. At the end of the 15 cycles, the PCR mixture incubated at 72° C. for 5 minutes and then held at 4° C. until removed from incubation and the PCR products purified. The PCR products from the PCR mixture are purified using a PCR clean up column from Qiagen.

In accordance with an embodiment of the present disclosure, another method for isolating and preparing libraries of target nucleic acid sequences uses a target isolation flap probe. In such an embodiment, nucleic acid sequences from sources of interest are extracted and purified from sources of interest where the nucleic acid sequences are hypothesized to contain the target sequences. For DNA extraction from cells, the cells are first breached or broken apart either physically by using, for example, the use of small beads at high velocities, or chemically by using, for example, detergents and other surfactants. An alcohol or other chemical is used for precipitating the DNA. The purified DNA is then treated, creating a pool of random DNA fragments.

Next, the random DNA fragments are combined with artificially created RNA sequences where these RNA sequences are complementary to repetitive sequences found in DNA. The artificially created RNA sequences are hereinafter referred to as "blocking RNA." The random DNA fragments and blocking RNA are heated to allow denaturation of the random DNA fragments and blocking RNA and then cooled to allow the blocking RNA to hybridize to the random DNA fragments.

Flap probes, containing the target-isolation sequences, with a biotin domain, is designed from the target sequences, where the flap probe contains a 5' region of single stranded DNA substantially complementary to the target sequence and a 5' protecting group that inhibited 5' nucleases. The flap probes contained a double-stranded 3' region formed by a hairpin structure on the 3' end of the flap probes. In one embodiment, the structure may be formed by the addition of a short, complementary strand to the 3' end of the probes. The 3' region contained an NGS platform specific sequencing primer site, a library amplification primer site and a barcode for sample identification. The flap probes are then added to a hybridization mixture containing the pool of random DNA fragments. In one embodiment, hybridization conditions consist of a hybridization buffer, e.g., 5×SSPE, 5× Deinhardt's, 0.1% SDS. Other hybridization buffers may be used in other embodiments. In one embodiment, a hybridization period may be, for example, sixteen (16) hours. However, such hybridization period may be greater or less in other embodiments depending upon the hybridization conditions.

The hybridization mixture containing the flap probes and random DNA fragments with subsections of the random DNA fragments hybridized to the blocking RNA is then incubated to allow one or more copies of the flap probes to hybridize to one or more copies of a target fragments.

A plurality of magnetic beads coated in streptavidin is added after the hybridization incubation. The hybridization solution is then incubated for approximately 30 minutes at ambient temperature. The plurality of magnetic beads is first isolated in the mixture using a magnetic source then separated from the hybridization solution, with the hybridization solution and non-target fragments discarded.

The plurality of magnetic beads, now associated with one or more of the target isolation sequences hybridized to one or more of the template fragments, are then washed with a buffer and resuspended in a 5' single-stranded nuclease buffer [10 mM Bis-Tris-Propane, 10 mM Mg Cl$_2$, 1 mM DTT, pH 7.0]. RNase H, a flap endonuclease (e.g., Fen-1), and T4 DNA ligase are added to the nuclease mixture. The nuclease mixture is incubated for 60 minutes at 25° C. The plurality of magnetic beads is then isolated from the nuclease mixture using a magnetic source and separated from the exonuclease mixture, with the exonuclease mixture being discarded.

The plurality of magnetic beads are then washed with a buffer and resuspended in an exonuclease buffer [10 mM Bis-Tris-Propane, 10 mM Mg Cl$_2$, 1 mM DTT, pH 7.0]. One or more single stranded 3' exonucleases (in one embodiment, Exonuclease T and Exonuclease I are added) are added to the exonuclease mixture. The exonuclease mixture is incubated for 30 minutes at 25° C. The plurality of magnetic beads is then isolated from the exonuclease mixture using a magnetic source and separated from the exonuclease mixture, with the exonuclease mixture being discarded.

The plurality of magnetic beads is then washed with a buffer and resuspended in a ligation buffer [66 mM Tris-HCl, 10 mM MgCl$_2$, 1 mM DTT, 1 mM ATP, 6% PEG 8000, pH 7.6]. A 3' adaptor sequence, with at least one double stranded region and T4 DNA ligase are then added and the ligation mixture is incubated for 15 minutes at ambient temperature. The 3' adaptor sequence contained an NGS platform-specific sequencing primer site, a library amplification site and a unique strand identifier. The plurality of magnetic beads is then isolated from the ligation mixture using a magnetic source and separated from the second ligation mixture, with the ligation mixture being discarded.

The plurality of magnetic beads is then washed with a buffer and resuspended in a PCR mixture containing water, a PCR master mix and amplification primers. The PCR cycling conditions are used as follows: 95° C. for 2 minutes followed by 15 cycles of 95° C. for 30 seconds, 60° C. for 30 seconds and 72° C. for 1 minute. At the end of the 15 cycles, the PCR mixture incubated at 72° C. for 5 minutes and then held at 4° C. until removed from incubation and the PCR products purified. The PCR products from the PCR mixture are purified using a PCR clean up column from Qiagen.

Attached hereto hare Attachments A-D that further describe methods in accordance with the present disclosure. In this regard, Attachment A describes a method for genome selection and conversion, which is hereinafter referred to as "variation 1." Variation 1 comprises a plurality of steps indicated on Pages 1-4 of Attachment A, and Pages 5, 6 are corresponding figures representing an exemplary process described by the plurality of steps. Note that the steps 1-27 are exemplary, and additional or fewer steps using different criteria may be used in other embodiments.

Attachment B describes a method for genome selection and conversion, which is hereinafter referred to as "variation 2." Variation 2 comprises a plurality of steps indicated on Page 1-3 of Attachment B, and Pages 5, 6 are corresponding figures representing an exemplary process described by the plurality of steps. Note that the steps 1-24 are exemplary, and additional or fewer steps using different criteria may be used in other embodiments.

Attachment C describes a method for genome selection and conversion, which is hereinafter referred to as "variation 3." Variation 3 comprises a plurality of steps indicated on Page 1-3 of Attachment C, and Page 4 is a corresponding figure representing an exemplary process described by the plurality of steps. Note that the steps 1-23 are exemplary, and additional or fewer steps using different criteria may be used in other embodiments.

Attachment D describes a method for genome selection and conversion, which is hereinafter referred to as "variation 4." Variation 4 comprises a plurality of steps indicated on Page 1-2 of Attachment D, and Page 3 is a corresponding figure representing an exemplary process described by the plurality of steps. Note that the steps 1-17 are exemplary, and additional or fewer steps using different criteria may be used in other embodiments.

What is claimed is:

1. A method for enriching for target nucleic acid sequences from a mixed population of nucleic acid fragments using a blocking RNA, a single labeled target isolation probe and two adaptor molecules, the method comprising:

(a) obtaining a population of nucleic acid fragments;

(b) adding to the population of nucleic acid fragments, the blocking RNA that hybridizes to nontarget repetitive sequences;

(c) denaturing double stranded nucleic acid into single stranded nucleic acids and permitting the blocking RNA to hybridize to the single stranded nucleic acids to form RNA blocked nucleic acid;

(d) hybridizing to the target nucleic acid sequence contained in the RNA blocked nucleic acid, the labeled target isolation nucleic acid probe, wherein the label is positioned between the 5' end and the 3' end of the labeled probe;

(e) immobilizing the hybridized nucleic acid of (d) by means of the label and removing unbound material;

(f) removing from the target nucleic acid sequences, non target nucleic acid sequences at the 3' end and the 5' end of the nucleic acid fragments of (e) by means of a 5' single strand specific exonuclease and a 3' single strand specific exonuclease or a single 3', 5' single strand specific exonuclease; and (g) ligating a 5' adaptor nucleic acid to the 3' end of the target nucleic acid sequence and a 3' adaptor nucleic acid to the 5' end of the target molecule either in parallel or sequentially and amplifying the target nucleic acid sequence therebetween.

* * * * *